(12) United States Patent
Van Liere

(10) Patent No.: US 11,707,288 B2
(45) Date of Patent: Jul. 25, 2023

(54) HEAT SINKS FOR CATHETERS, AND SYSTEMS AND METHODS THEREOF

(71) Applicant: C. R. Bard, Inc., Franklin Lakes, NJ (US)

(72) Inventor: Chad Van Liere, Phoenix, AZ (US)

(73) Assignee: C.R. Bard, Inc., Franklin Lakes, NJ (US)

(*) Notice: Subject to any disclaimer, the term of this patent is extended or adjusted under 35 U.S.C. 154(b) by 455 days.

(21) Appl. No.: 16/759,897

(22) PCT Filed: Nov. 10, 2017

(86) PCT No.: PCT/US2017/061083
§ 371 (c)(1),
(2) Date: Apr. 28, 2020

(87) PCT Pub. No.: WO2019/094028
PCT Pub. Date: May 16, 2019

(65) Prior Publication Data
US 2021/0059698 A1     Mar. 4, 2021

(51) Int. Cl.
*A61B 17/22*    (2006.01)
*A61B 17/00*    (2006.01)

(52) U.S. Cl.
CPC .......... *A61B 17/22012* (2013.01); *A61B 2017/00477* (2013.01); *A61B 2017/22015* (2013.01)

(58) Field of Classification Search
CPC ......... A61B 2017/320088; A61B 2017/22015; A61B 17/22012; A61B 2017/22014;
(Continued)

(56) References Cited

U.S. PATENT DOCUMENTS

| | | | |
|---|---|---|---|
| 7,604,608 B2 | 10/2009 | Nita et al. | |
| 8,226,629 B1 | 7/2012 | Keilman et al. | |

(Continued)

FOREIGN PATENT DOCUMENTS

| | | |
|---|---|---|
| JP | H09-294744 A | 11/1997 |
| JP | 2001-321388 A | 11/2001 |

(Continued)

OTHER PUBLICATIONS

Office Action dated Feb. 8, 2023 pertaining to Chinese Patent Application 201780097616.7.

(Continued)

*Primary Examiner* — Thomas McEvoy
(74) *Attorney, Agent, or Firm* — Dinsmore & Shohl LLP

(57) ABSTRACT

A catheter assembly including, in some embodiments, a sonic connector at a proximal end of a core wire, a damping mechanism around a proximal end portion of the core wire, and a heat sink connected to the damping mechanism. The sonic connector is configured to couple to an ultrasound-producing mechanism and transmit vibrational energy to the proximal end of the core wire, which core wire includes a distal end portion configured to modify intravascular lesions. The damping mechanism includes a gasket system around the proximal end portion of the core wire in a damping-mechanism bore of the catheter assembly. The damping mechanism is configured to damp the vibrational energy. A system including, in some embodiments, the catheter assembly and the ultrasound-producing mechanism is also disclosed.

17 Claims, 11 Drawing Sheets

Figure 1:
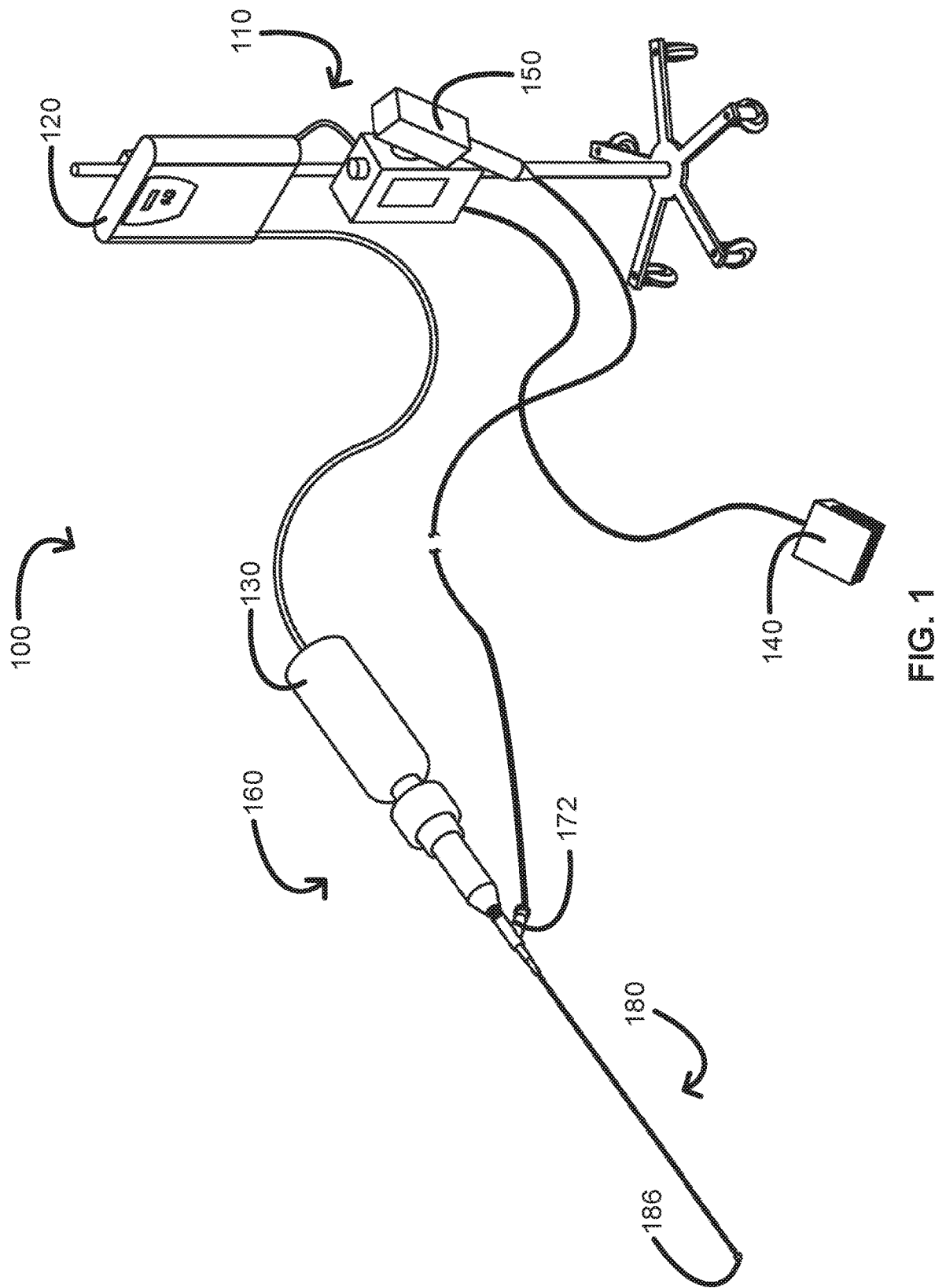

(58) Field of Classification Search
CPC .... A61B 2017/22027; A61B 17/22004; A61B 17/320068; A61B 2017/320069; A61B 17/320092; A61B 2017/320093; A61B 2017/320094; A61B 2017/320095; A61B 2017/320098; A61B 17/3201; A61B 2017/320082; A61B 2017/320072; A61B 2017/320073; A61B 2017/320074; A61B 2017/320075; A61B 2017/320077; A61B 2017/320078; A61B 2017/32008; A61B 2017/320071; A61B 2017/32007
See application file for complete search history.

(56) References Cited

U.S. PATENT DOCUMENTS

| | | | |
|---|---|---|---|
| 8,961,423 | B2 | 2/2015 | Nita et al. |
| 2004/0167507 | A1* | 8/2004 | Nita ................. A61B 17/22012 606/27 |
| 2006/0047239 | A1 | 3/2006 | Nita |
| 2016/0113699 | A1 | 4/2016 | Sverdlik et al. |
| 2017/0007855 | A1* | 1/2017 | Toda .............. A61B 17/320068 |

FOREIGN PATENT DOCUMENTS

| | | |
|---|---|---|
| JP | 2002-522934 A | 7/2002 |
| JP | 2006519054 A | 8/2006 |
| JP | 2008510573 A | 4/2008 |
| WO | 2000008630 A1 | 2/2000 |
| WO | 2004075945 W | 9/2004 |
| WO | 2006026207 W | 3/2006 |
| WO | WO 2016/009788 * | 1/2016 |

OTHER PUBLICATIONS

Office Action, dated Apr. 4, 2023, pertaining to Japanese Application No. 2022-062997.

* cited by examiner

HEAT SINKS FOR CATHETERS, AND SYSTEMS AND METHODS THEREOF

RELATED APPLICATIONS

This application is a U.S. national phase of International Application No. PCT/US2017/061083 filed Nov. 10, 2017, which is incorporated herein by reference in its entirety.

BACKGROUND

Atherosclerosis is characterized by one or more intravascular lesions formed, in part, of plaque including blood-borne substances such as fat, cholesterol, or calcium. An intravascular lesion such as an arterial lesion can form on a wall of an arterial lumen and build out across the lumen to an opposite arterial wall. A last point of patency often occurs at a boundary between the arterial lesion and the opposite arterial wall. Surgical procedures for atherosclerosis such as atherectomy can be used to restore patency and blood flow impeded by such lesions. However, prolonged running times required of endoluminal devices such as catheters for modification of intravascular lesions can lead to heat-related complications for the endoluminal devices, which, in turn, can lead to complications in the surgical procedures and the patients undergoing the surgical procedures. Provided herein in some embodiments are heat sinks for catheters, as well as systems and methods thereof that address at least the foregoing.

SUMMARY

Provided herein is a catheter assembly including, in some embodiments, a sonic connector at a proximal end of a core wire, a damping mechanism around a proximal end portion of the core wire, and a heat sink connected to the damping mechanism. The sonic connector is configured to couple to an ultrasound-producing mechanism and transmit vibrational energy to the proximal end of the core wire, which core wire includes a distal end portion configured to modify intravascular lesions. The damping mechanism includes a gasket system around the proximal end portion of the core wire in a damping-mechanism bore of the catheter assembly. The damping mechanism is configured to damp the vibrational energy.

In some embodiments, the heat sink includes a first sleeve around the gasket system and a second sleeve around the first sleeve. The first sleeve is of a first material having a first thermal conductivity, and the second sleeve is of a second material having a second thermal conductivity greater than the first thermal conductivity.

In some embodiments, the second sleeve is configured as a passive heat exchanger. The heat exchanger includes a number of circumferential fins arranged along a length of the second sleeve configured to dissipate the heat from the damping mechanism. Alternatively, the heat exchanger includes a number of longitudinal fins arranged around a circumference of the second sleeve configured to dissipate the heat from the damping mechanism.

In some embodiments, the first sleeve includes a cavity formed by a circumferential groove around the first sleeve. The cavity is filled with a coolant, and the second sleeve is disposed over the cavity.

In some embodiments, the coolant is water, a glycol, a water-glycol mixture, a mineral oil, a silicone oil, or a heat-storage material.

In some embodiments, the heat sink includes a first annulus at a first end of the gasket system, a second annulus at a second, opposing end of the gasket system, and a number of longitudinal members arranged around a circumference of the gasket system.

In some embodiments, a center of the gasket system is positioned over a vibrational node of the core wire where the core wire experiences less transverse-wave-producing vibrational energy than an anti-node of the core wire, thereby reducing frictional heating.

In some embodiments, the gasket system includes a number of axially and radially compressed O-rings in the damping-mechanism bore.

In some embodiments, a polymeric sleeve is around an exposed portion of the proximal end portion of the core wire between the sonic connector and a retainer configured to retain the O-rings in the damping-mechanism bore.

In some embodiments, the polymeric sleeve is around the exposed portion of the proximal end portion of the core wire and further around the proximal end portion of the core wire in the damping mechanism.

In some embodiments, the catheter assembly further includes at least a portion of an ultrasound-producing mechanism including an ultrasound transducer.

Also provided herein is a system including, in some embodiments, a catheter assembly and an ultrasound-producing mechanism. The catheter assembly includes a sonic connector at a proximal end of a core wire, a damping mechanism around a proximal end portion of the core wire, and a heat sink connected to the damping mechanism. The sonic connector is configured to transmit vibrational energy to the proximal end of the core wire, which core wire includes a distal end portion configured to modify intravascular lesions. The damping mechanism includes a gasket system around the proximal end portion of the core wire in a damping-mechanism bore of the catheter assembly. The damping mechanism is configured to damp the vibrational energy. The ultrasound-producing mechanism includes an ultrasound generator and an ultrasound transducer.

In some embodiments, the heat sink includes a first sleeve around the gasket system and a second sleeve around the first sleeve. The first sleeve is of a first material having a first thermal conductivity, and the second sleeve is of a second material having a second thermal conductivity greater than the first thermal conductivity.

In some embodiments, the second sleeve is configured as a passive heat exchanger. The heat exchanger includes a number of circumferential fins arranged along a length of the second sleeve configured to dissipate the heat from the damping mechanism. Alternatively, the heat exchanger includes a number of longitudinal fins arranged around a circumference of the second sleeve configured to dissipate the heat from the damping mechanism.

In some embodiments, the first sleeve includes a cavity formed by a circumferential groove around the first sleeve. The cavity is filled with a coolant selected from water, a glycol, a water-glycol mixture, a mineral oil, a silicone oil, and a heat-storage material. The second sleeve is disposed over the cavity sealing the coolant in the cavity.

In some embodiments, the heat sink includes a first annulus at a first end of the gasket system, a second annulus at a second, opposing end of the gasket system, and a number of longitudinal members arranged around a circumference of the gasket system.

In some embodiments, the gasket system includes a number of axially and radially compressed O-rings in the damping-mechanism bore.

In some embodiments, a polymeric sleeve is around an exposed portion of the proximal end portion of the core wire between the sonic connector and a retainer configured to retain the O-rings in the damping-mechanism bore.

In some embodiments, the polymeric sleeve is around the exposed portion of the proximal end portion of the core wire and further around the proximal end portion of the core wire in the damping mechanism.

In some embodiments, the system further includes a console including a foot switch and the ultrasound-producing mechanism including both the ultrasound generator and the ultrasound transducer. The foot switch is configured to activate and deactivate the ultrasound-producing mechanism.

In some embodiments, the system further includes a console including a foot switch and only the ultrasound generator of the ultrasound-producing mechanism. The catheter assembly further includes the ultrasound transducer of the ultrasound-producing mechanism. The foot switch is configured to activate and deactivate the ultrasound-producing mechanism.

Also provided herein is a method for making a catheter assembly including, in some embodiments, molding a cartridge including a damping-mechanism bore in a first sleeve; disposing a second sleeve over the first sleeve to form a heat sink including the first and second sleeves; disposing a core wire through a center of the damping-mechanism bore coincident with a rotational axis of the cartridge; disposing a number of O-rings in the damping-mechanism bore around the core wire; and fixing a retainer in a proximal end of the damping-mechanism bore to form a damping mechanism around the core wire. Fixing the retainer in the proximal end of the damping-mechanism bore generates a compressive force on the core wire. The compressive force is sufficient for damping vibrational energy in a proximal end portion of the core wire.

In some embodiments, the method further includes disposing the core wire in a polymeric sleeve; and uniformly heating the polymeric sleeve to shrink the polymeric sleeve around the core wire before disposing the core wire through the center of the damping-mechanism bore.

In some embodiments, the method further includes molding a housing of a catheter assembly; disposing the cartridge with the damping mechanism and the heat sink in the housing of the catheter assembly; and connecting a proximal end of the core wire to an ultrasound-producing mechanism.

DRAWINGS

FIG. 1 provides a schematic illustrating a system in accordance with some embodiments.

Figure 2:
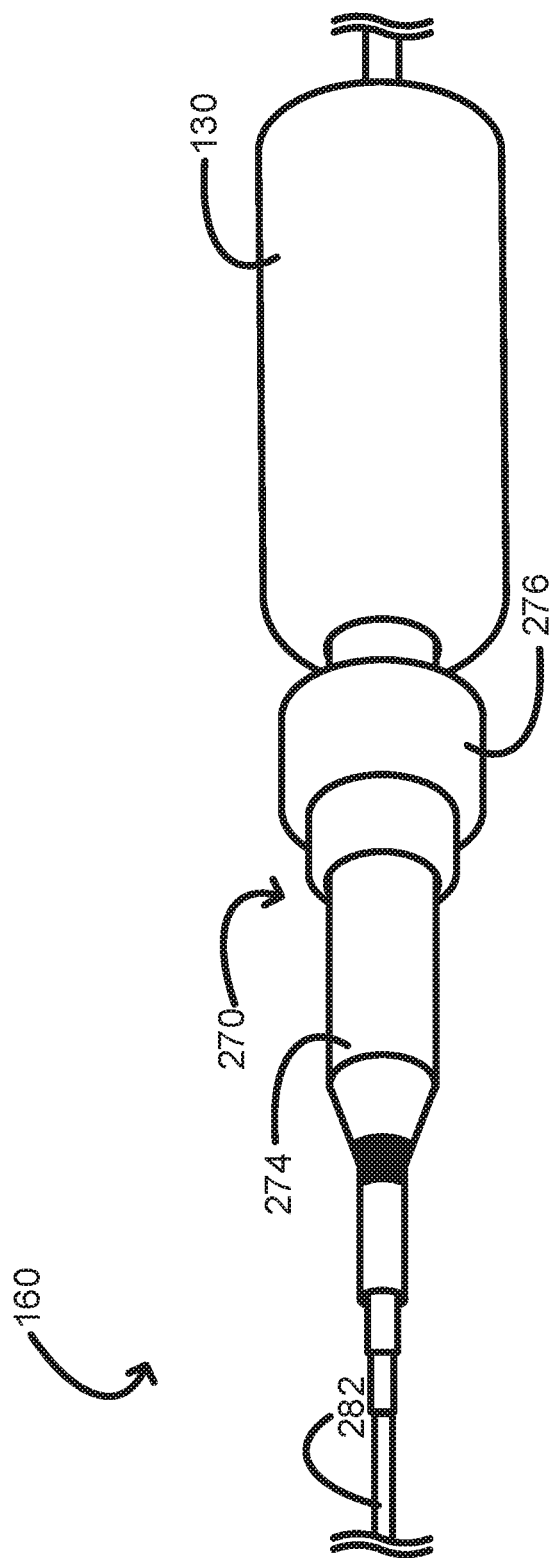

FIG. 2 provides a schematic illustrating a catheter assembly in accordance with some embodiments.

Figure 3A:
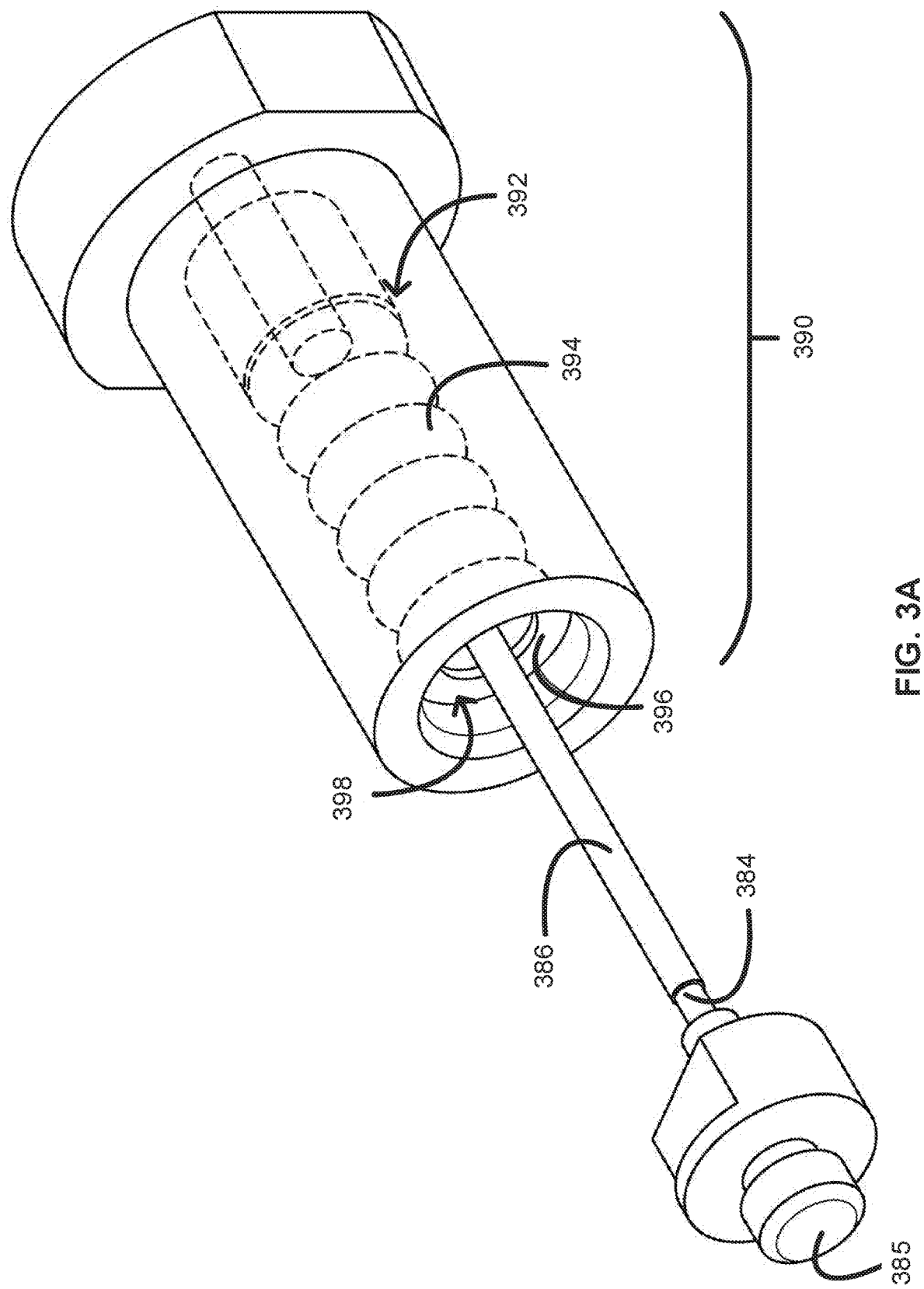

FIG. 3A provides a schematic illustrating an oblique view of cartridge including a damping mechanism in accordance with some embodiments.

Figure 3B:
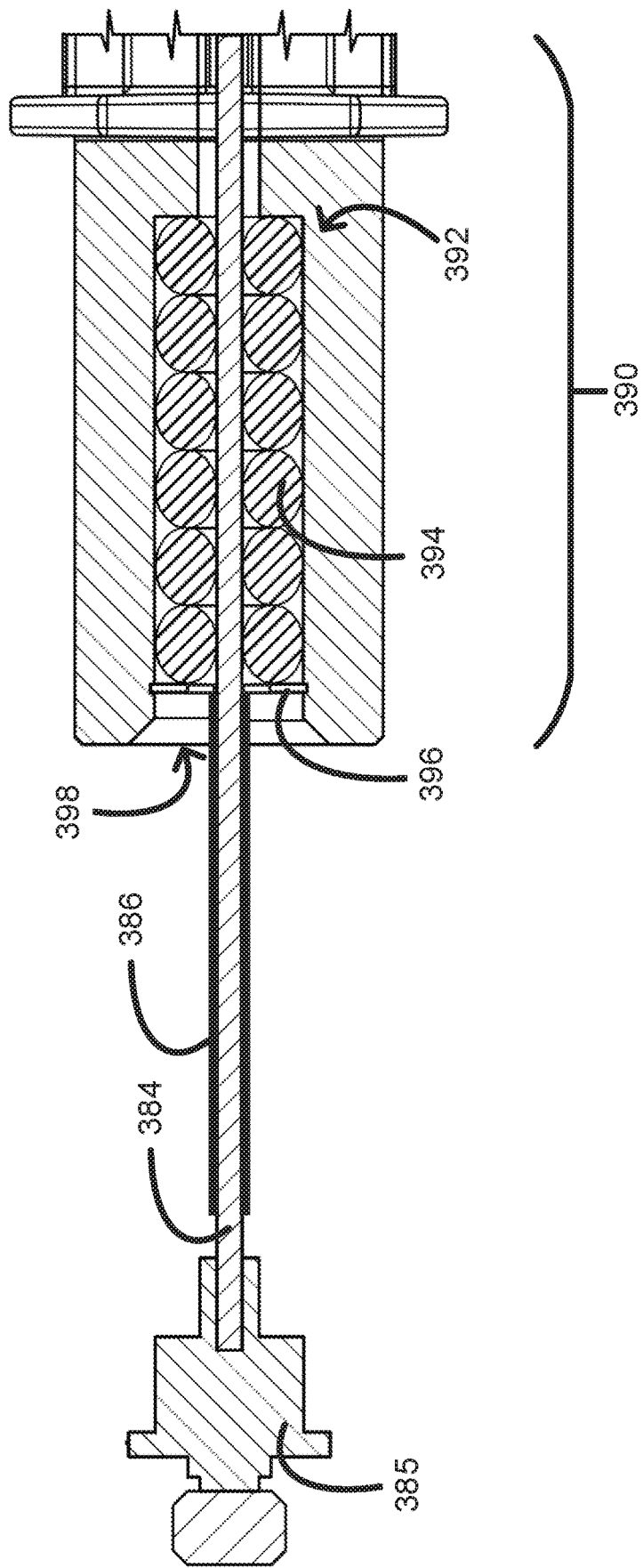

FIG. 3B provides a schematic illustrating a cross-sectional view of the cartridge including the damping mechanism of FIG. 3A.

Figure 4:
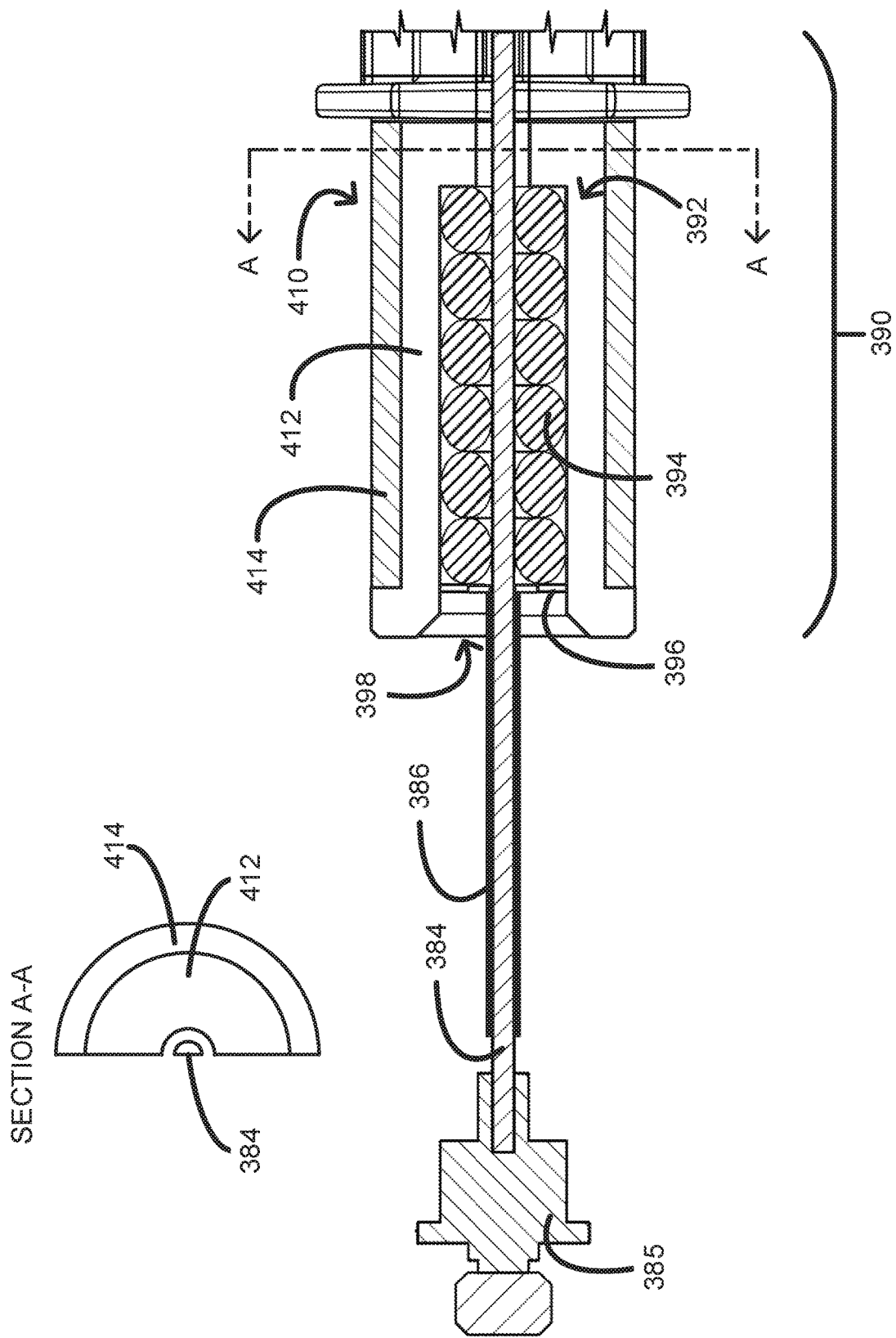

FIG. 4 provides a schematic illustrating a cross-sectional view of a damping mechanism and a first heat sink in accordance with some embodiments.

Figure 5A:
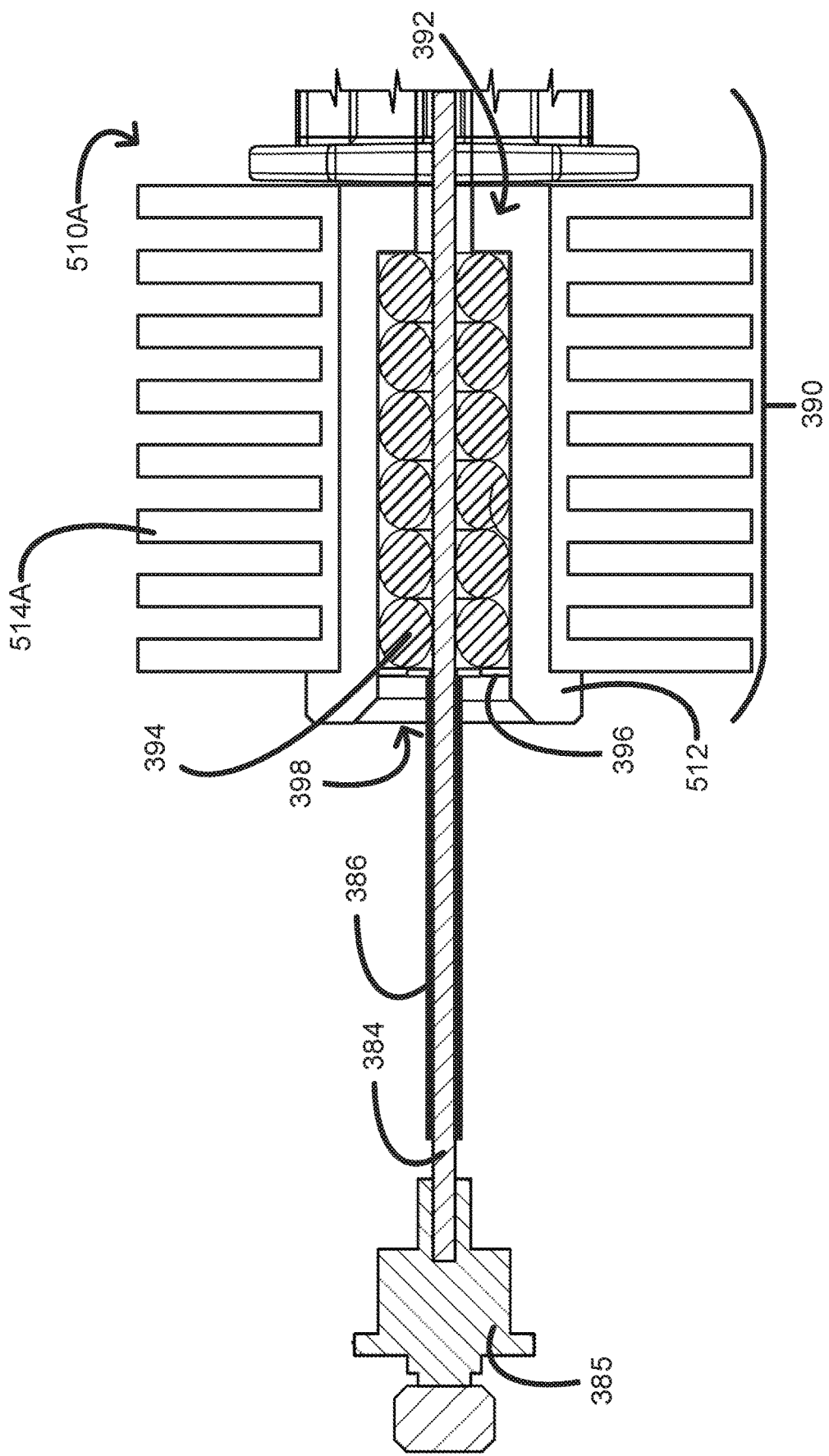

FIG. 5A provides a schematic illustrating a cross-sectional view of a damping mechanism and a second heat sink in accordance with some embodiments.

Figure 5B:
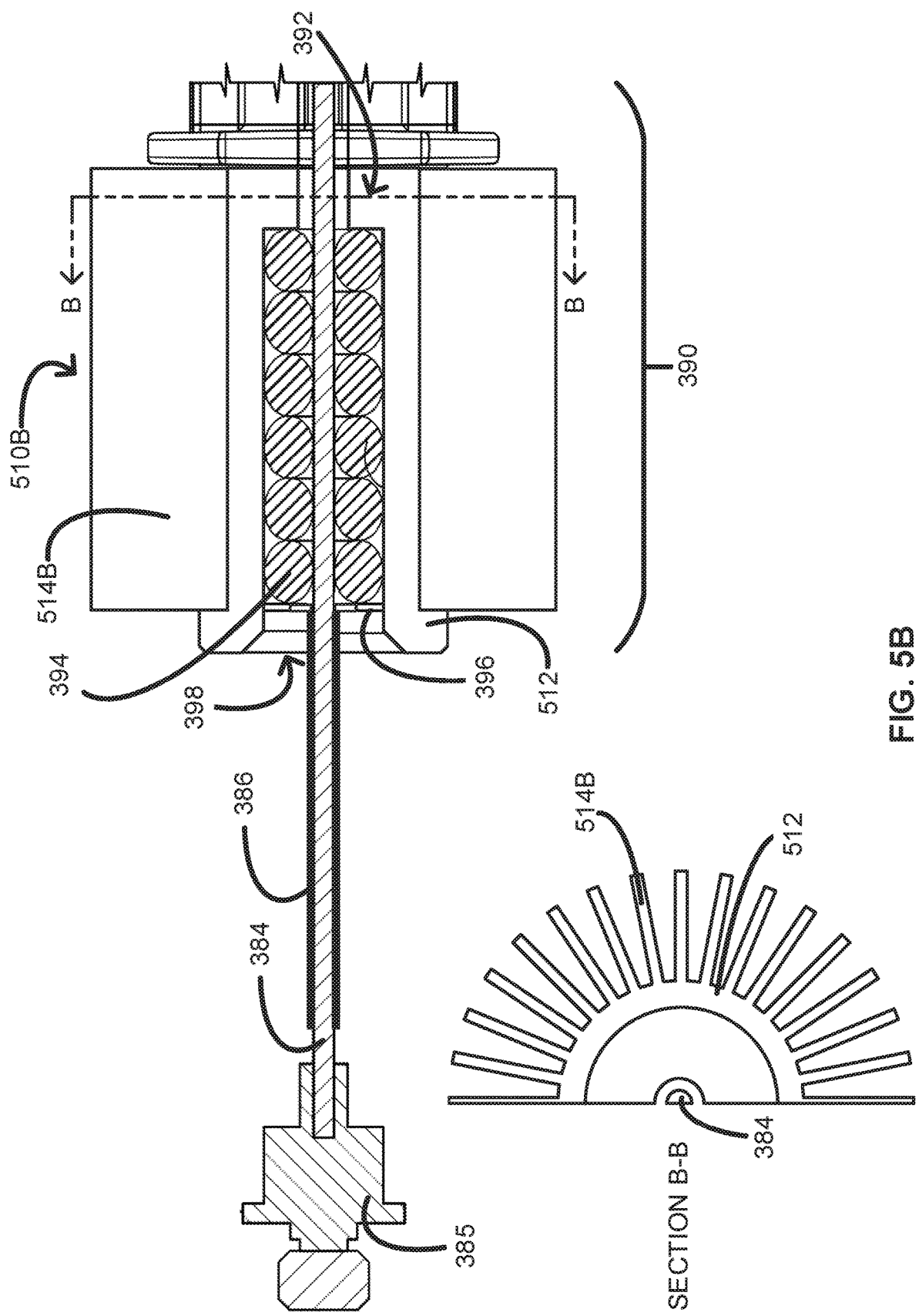

FIG. 5B provides a schematic illustrating a cross-sectional view of a damping mechanism and a third heat sink in accordance with some embodiments.

Figure 6:
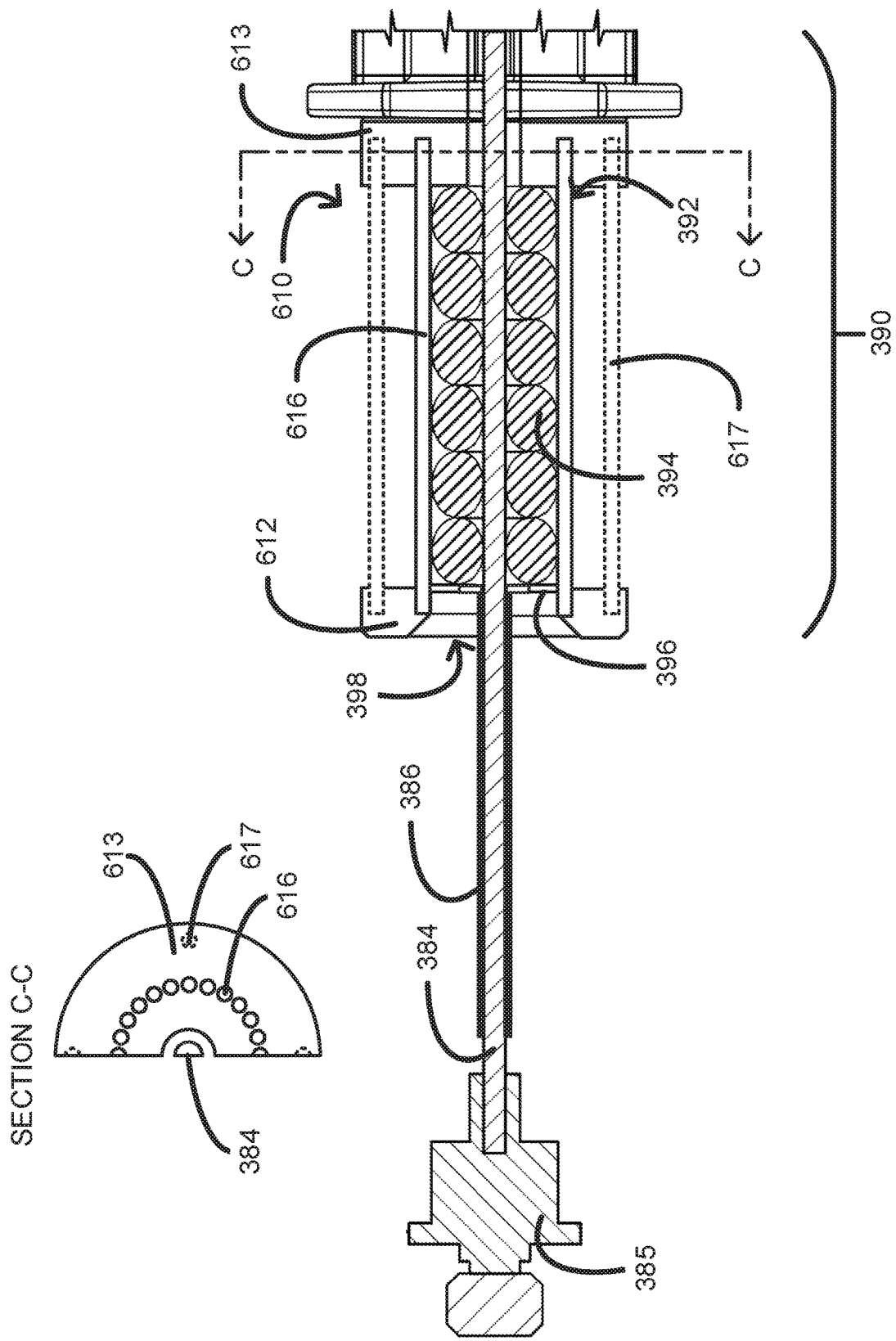

FIG. 6 provides a schematic illustrating a cross-sectional view of a damping mechanism and a fourth heat sink in accordance with some embodiments.

Figure 7:
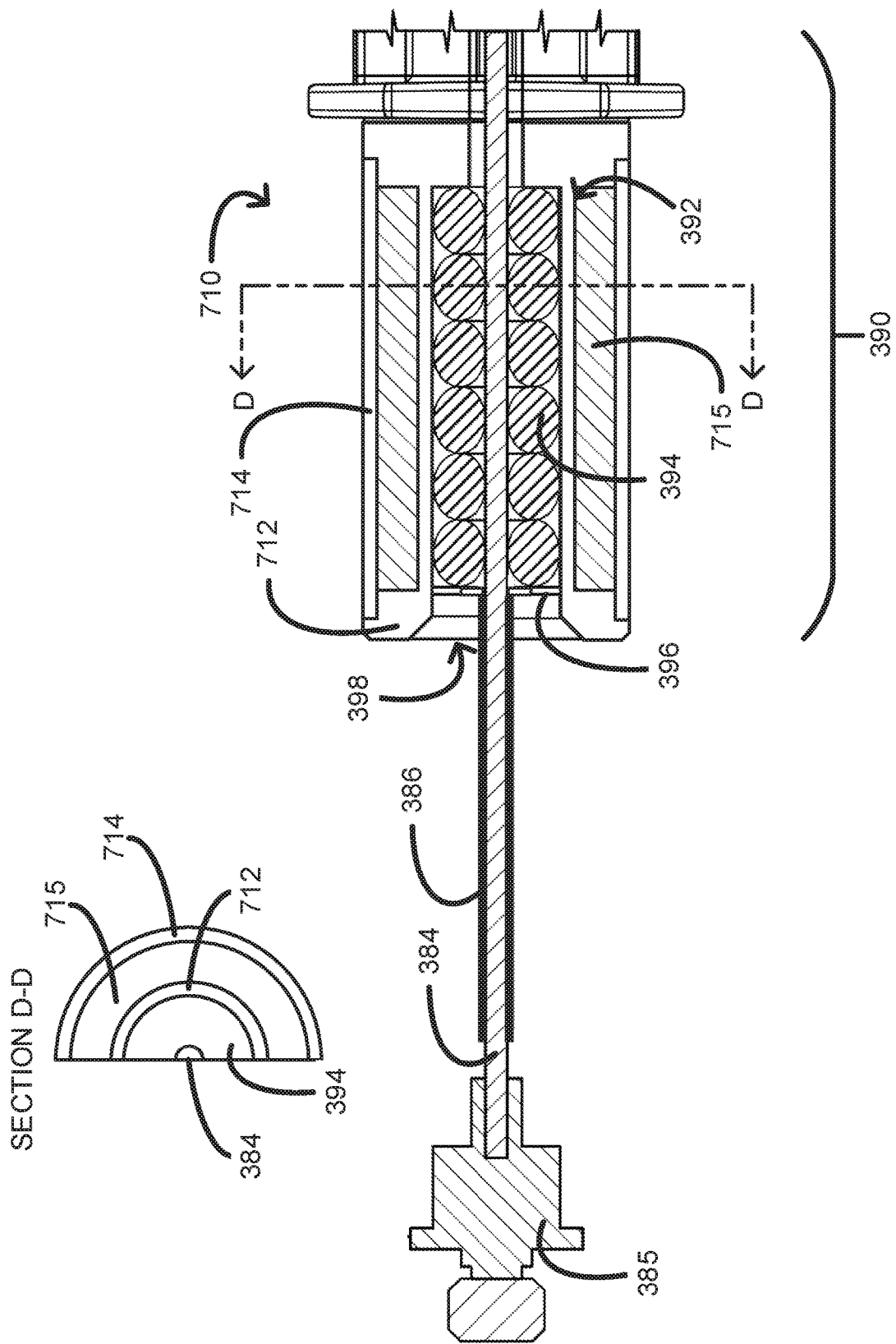

FIG. 7 provides a schematic illustrating a cross-sectional view of a damping mechanism and a fifth heat sink in accordance with some embodiments.

Figure 8A:
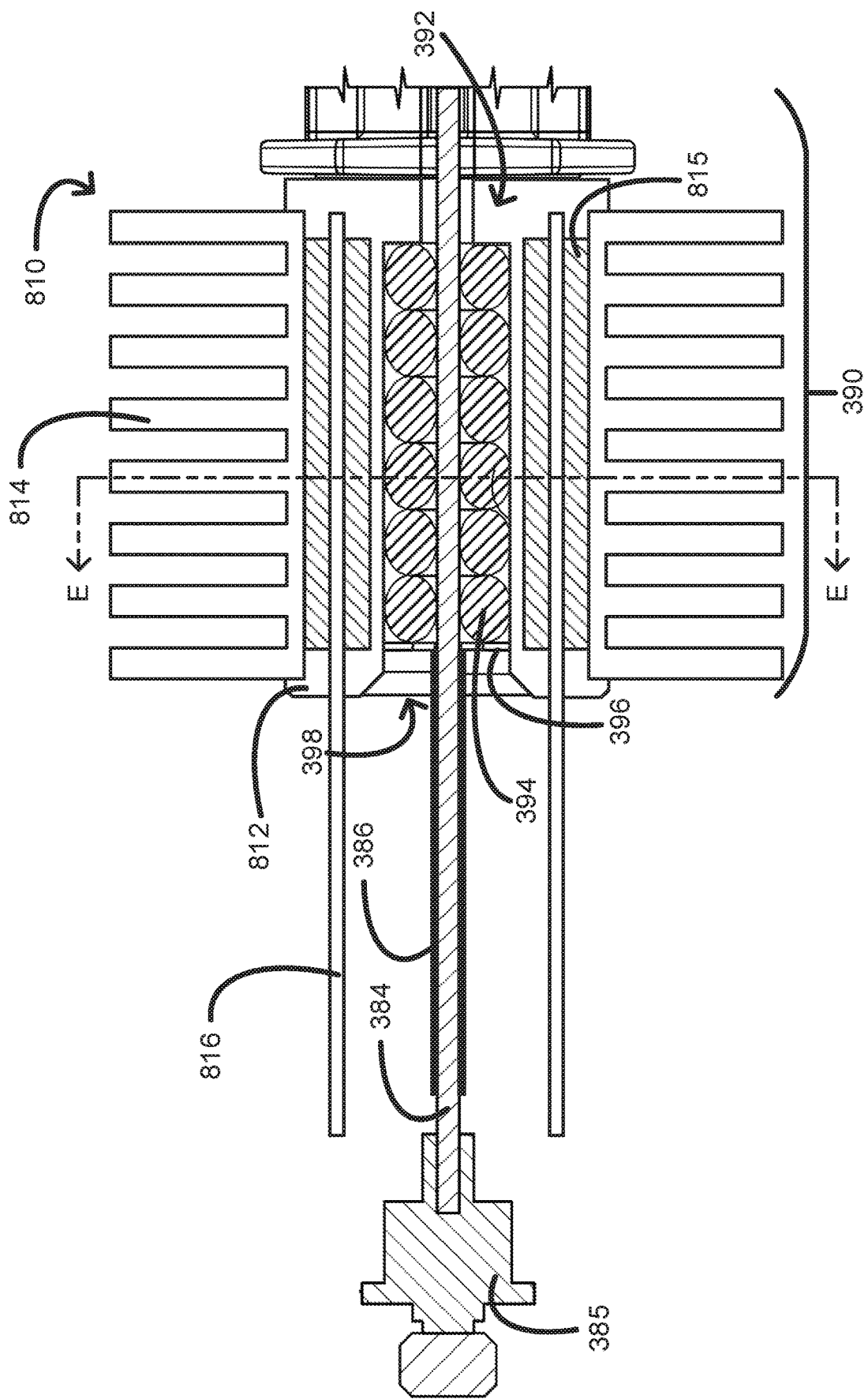

FIG. 8A provides a schematic illustrating a cross-sectional view of a damping mechanism and a sixth heat sink in accordance with some embodiments.

Figure 8B:
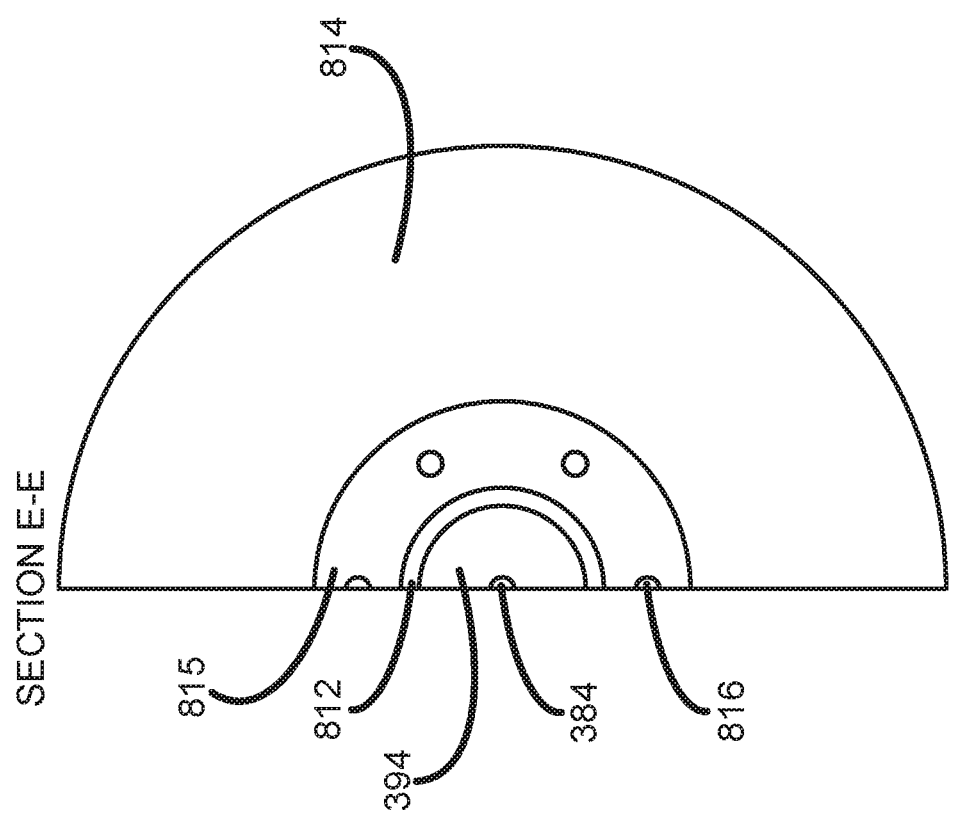

FIG. 8B provides a schematic illustrating a cross-sectional view (Section E-E) of the damping mechanism and the sixth heat sink of FIG. 8A.

DESCRIPTION

Before some particular embodiments are provided in greater detail, it should be understood that the particular embodiments provided herein do not limit the scope of the concepts provided herein. It should also be understood that a particular embodiment provided herein can have features that can be readily separated from the particular embodiment and optionally combined with or substituted for features of any of a number of other embodiments provided herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter provided herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter provided herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

The term "heat capacity" is used in association with a feature (e.g., the second sleeve 414) or a combination of features (e.g., the first heat sink 410) and its ability or resistance to change temperature from applied heat, which is an extrinsic physical property depending upon at least a size of the feature or the combination of features.

The term "specific heat capacity" is used in association with a material (e.g., the second material of the second sleeve 414) and its ability or resistance to change temperature from applied heat, which is an intrinsic physical property when the amount of the material is taken into consideration.

Unless defined otherwise, all technical and scientific terms used herein have the same meaning as commonly understood by those of ordinary skill in the art.

Atherosclerosis is characterized by one or more intravascular lesions formed, in part, of plaque including bloodborne substances such as fat, cholesterol, or calcium. An intravascular lesion such as an arterial lesion can form on a wall of an arterial lumen and build out across the lumen to an opposite arterial wall. A last point of patency often occurs at a boundary between the arterial lesion and the opposite arterial wall. Surgical procedures for atherosclerosis such as atherectomy can be used to restore patency and blood flow impeded by such lesions. However, prolonged running times required of endoluminal devices such as catheters for modification of intravascular lesions can lead to heat-related complications for the endoluminal devices, which, in turn, can lead to complications in the surgical procedures and the patients undergoing the surgical procedures. Provided herein in some embodiments are heat sinks for catheters, as well as systems and methods thereof that address at least the foregoing.

FIG. 1 provides a schematic illustrating a system 100 in accordance with some embodiments. The system 100 includes a console 110 coupled to a catheter assembly 160, which system 100 is configured for modifying intravascular lesions including crossing the intravascular lesions, ablating the intravascular lesions, or a combination of crossing and ablating the intravascular lesions.

As shown in FIG. 1, the system 100 includes the console 110. The console 110 provides to the system operator an instrument for monitoring and controlling the system 100 and various sub-systems and functions of the system 100. The console 110 includes an ultrasound-producing mechanism including an ultrasound generator 120 and an ultrasound transducer 130. Alternatively, the console 110 includes the ultrasound generator 120, the catheter assembly 160 includes the ultrasound transducer 130, and the ultrasound-producing mechanism is divided between the console 110 and the catheter assembly 160. The ultrasound-producing mechanism is configured to convert an electric current into vibrational energy. For example, the ultrasound generator 120 is configured to convert an alternating electric current (e.g., a current associated with mains electricity) into a high-frequency current (e.g., a current with a frequency commensurate with the operating frequency of the ultrasound transducer 130), and the ultrasound transducer 130, in turn, is configured to convert the high-frequency current into the vibrational energy (e.g., >20 kHz such as 20.5 kHz±500 Hz).

The console 110 optionally further includes a foot switch 140 configured to activate and deactivate the system 100 such as activate and deactivate at least the ultrasound-producing mechanism and any components thereof or any components coupled thereto. When the system 100 is powered, the foot switch 140 is used to activate or deactivate the system 100, thereby activating or deactivating components of the ultrasound-producing mechanism such as the ultrasound transducer 130; components coupled to the ultrasound-producing mechanism, such as a core wire 384 and a tip or tip member 186 of the core wire 384 (see FIGS. 3A and 3B); or combinations thereof.

The console 110 optionally further includes an injector 150 configured to inject an irrigant into an irrigation port 172 of the catheter assembly 160. The irrigant includes, for example, a sterile liquid (e.g., water, saline, heparinized saline, etc.) for irrigating an anatomical area undergoing an intravascular-lesion-modifying procedure (e.g., crossing an intravascular lesion, ablating an intravascular lesion, etc.), for cooling the core wire 384 of the catheter assembly 160, or a combination thereof.

The console 110 optionally further includes both the foot switch 140 and the injector 150. In such embodiments, the foot switch 140 can be further configured to activate and deactivate the injector 150 when the system 100 is respectively activated and deactivated with the foot switch 140.

FIG. 2 provides a schematic illustrating the catheter assembly 160 in accordance with some embodiments. The catheter assembly 160 includes a housing 270 coupled to a catheter body 180 (see FIG. 1) including a sheath 282, the core wire 384 (see FIGS. 3A and 3B) disposed in a lumen of the sheath 282, and the tip or tip member 186, which catheter assembly 160 is configured for modifying intravascular lesions including crossing the intravascular lesions, ablating the intravascular lesions, or a combination of crossing and ablating the intravascular lesions.

As shown in FIG. 2, the housing 270 includes a hub 274 and a lock collar 276 for locking the housing 270 onto the ultrasound transducer 130. (The irrigation port 172 is not shown in FIG. 2, as the irrigation port 172 is optional in some embodiments.) Locking the housing 270 onto the ultrasound transducer 130 ensures a proximal end of the core wire 384 is sufficiently vibrationally coupled to the ultrasound transducer 130 for modifying intravascular lesions. The proximal end of the core wire 384 is vibrationally coupled to the ultrasound transducer 130 by a sonic connector 385 (see FIGS. 3A and 3B), optionally through an intervening ultrasound horn, and a distal end of the core wire 384 is vibrationally coupled to a lesion-modifying tip 186 fashioned from the distal end of the core wire 384 or a lesion-modifying tip member 186 coupled to the distal end of the core wire 384. As such, the sonic connector 385 is configured to impart or otherwise transfer the vibrational energy from the ultrasound transducer 130 to the core wire 384. And the core wire 384 is configured to impart or otherwise transfer the vibrational energy to the tip or tip member 186 of the core wire 384 for modifying intravascular lesions. Again, the catheter assembly 160 alternatively includes the ultrasound transducer 130, which divides the ultrasound-producing mechanism between the console 110 and the catheter assembly 160. In such embodiments, the housing 270 further includes the ultrasound transducer 130 disposed therein at the proximal end of the core wire 384, thereby obviating the lock collar 274 shown in FIG. 2.

A working length of a distal end portion of the core wire 384 beyond the sheath 282 or the lumen of the sheath 282 is configured to displace for intravascular lesion modification. The displacement includes at least longitudinal, transverse, or longitudinal and transverse displacement in accordance with a profile of the core wire 384 and the vibrational energy (e.g., >20 kHz such as 20.5 kHz±500 Hz). Longitudinal displacement of the working length of the core wire 384 results in micromotion such as cavitation, and transverse displacement of the working length of the core wire 384 results in macromotion. The micromotion is used to cross intravascular lesions. The macromotion coupled with the micromotion is used to ablate intravascular lesions, thereby breaking the lesions into minute fragments and restoring patency and blood flow.

FIG. 3A provides a schematic illustrating an oblique view of a cartridge 390 including a damping mechanism 392 in accordance with some embodiments. FIG. 3B provides a schematic illustrating a cross-sectional view of the cartridge 390 including the damping mechanism 392 of FIG. 3A. The damping mechanism 392 includes a gasket system 394 configured to exert a compressive force around a proximal end portion of the core wire 384 and a retainer 396 configured to retain the gasket system 394 within a damping-mechanism bore 398 of the cartridge 390 of the catheter assembly 160.

As shown in FIGS. 3A and 3B, the gasket system 394 includes a number of O-rings, which range from 1 O-ring to 12 O-rings, including 2 to 10 O-rings, such as 2 to 6 O-rings, for example, 2 to 4 O-rings. In some embodiments, for example, the number of O-rings is 2, 4, 6, or 8 O-rings. The O-rings are axially compressed and retained in the damping-mechanism bore 398 by the retainer 396 (e.g., a washer such as a retaining washer, for example, an external star washer). Axial compression of the O-rings by the retainer 396 generates a radial compression by an inner wall of the damping-mechanism bore 398 on the core wire 384 sufficient to damp a number of degrees of freedom of vibrational energy provided by the ultrasound-producing mechanism not needed for modifying intravascular lesions. For example, transverse-wave-producing vibrational energy about the proximal end portion of the core wire 384 can be damped in favor of the longitudinal-wave-producing vibrational energy.

In embodiments of the system 100 including the injector 150, the gasket system 394 prevents irrigation backflow of the irrigant through the catheter assembly 160 such as through the damping mechanism 392 and into the ultrasound transducer 130 of the ultrasound-producing mechanism.

The damping mechanism 392 further includes a sleeve 386 around the core wire 384. The sleeve 386 is around at least the proximal end portion of the core wire 384 between the sonic connector 385 and the retainer 396. If not encased by the sleeve 386, the core wire 384 would include an exposed portion of the proximal end portion of the core wire 384 between the sonic connector 385 and the retainer 396. The sleeve 386 around the proximal end portion of the core wire 384 between the sonic connector 385 and the retainer 396 prevents fatigue of the core wire 384. The sleeve 386 can be further around at least the proximal end portion of the core wire 384 within the damping mechanism 392, as well as around the core wire 384 distal to the damping mechanism 392 up to at least a length of the core wire 384 at which the working length of the core wire 384 begins.

The sleeve 386 around the core wire 384 encases the core wire 384 with an engineering fit selected from a clearance fit, a transition fit, and an interference fit. The clearance fit is a fairly loose fit that enables the core wire 384 to freely rotate or slide within the sleeve 386; the transition fit firmly holds the core wire 384 in place within the sleeve 386, but not so firmly that the core wire 384 cannot be removed from the sleeve 386; and the interference fit securely holds the core wire 384 in place within the sleeve 386 such that the core wire 384 cannot be removed from the sleeve 386 without damaging the core wire 384, the sleeve 386, or both. In some embodiments, the sleeve 386 encases the core wire 384 with a transition fit or an interference fit. The transition fit and the interference fit are created by, for example, heat-shrinking a suitably sized sleeve for the desired fit about the core wire 384 during assembly of the catheter assembly 160. The sleeve 386 around the core wire 384 is a polymeric sleeve such as a polytetrafluoroethylene ("PTFE") sleeve.

Heat in the damping mechanism 392 of an activated catheter assembly can build up quickly, particularly in disposable or single-use disposable catheter assemblies such as the catheter assembly 160 in some embodiments. Such disposable catheter assemblies cannot use typical heat exchange systems such as pipes, pumps, fans, or combinations thereof. In addition, temperature-measuring devices for the damping mechanism 392 such as thermocouples, on-board microprocessors, or printed circuit boards are cost prohibitive. The damping mechanism 392 can be centered over a vibrational node of the core wire 384, or the core wire 384 can be adjusted such that the damping mechanism 392 is over a vibrational node of the core wire 384. This reduces some heat caused by damping the vibrational energy because the core wire experiences less transverse-wave-producing vibrational energy at the vibrational node of the core wire than at an anti-node of the core wire. However, heat sinks for catheter assemblies such as the heat sinks provided herein are more effective than centering alone at reducing the heat, reducing the temperature in activated catheter assemblies by at least about 80° F.

FIG. 4 provides a schematic illustrating a cross-sectional view of the damping mechanism 392 and a first heat sink 410 in accordance with some embodiments. The heat sink 410 includes a first sleeve 412 around the gasket system 392 and a second sleeve 414 around the first sleeve 412.

The first sleeve 412 is of a first material having a first thermal conductivity, and the second sleeve 414 is of a second material having a second thermal conductivity greater than the first thermal conductivity. The first material of the first sleeve 412 can be a polymer such as polycarbonate, and the second material of the second sleeve 414 can be a different polymer (e.g., polyetherimide ["PEI"]), a metal (e.g., stainless steel), or an alloy. A radially oriented thermal gradient, or a thermal gradient vector field, is thereby established from the gasket system 392, through the first sleeve 412, through the second sleeve 414, and into a fluid medium (e.g., air within the housing 270) for conducting heat away from the damping mechanism 392. The thermal conductivity and thermal capacity of the heat sink 410 is such that the catheter assembly 160 can be operated for at least 5, 10, 15, 20, 25, or 30 minutes for modifying intravascular lesions.

FIG. 5A provides a schematic illustrating a cross-sectional view of the damping mechanism 392 and a second heat sink 510A in accordance with some embodiments. FIG. 5B provides a schematic illustrating a cross-sectional view of the damping mechanism 392 and a third heat sink 510B in accordance with some embodiments. The heat sink 510A includes a first sleeve 512 around the gasket system 392 and a second sleeve 514A around the first sleeve 512. Likewise, the heat sink 510B includes the first sleeve 512 around the gasket system 392 and a second sleeve 514B around the first sleeve 512.

As shown in FIGS. 5A and 5B, the second sleeve 514A of the heat sink 510A and the second sleeve 514B of the heat sink 510B are configured as passive heat exchangers. The second sleeve 514A is configured as a passive heat exchanger with a number of circumferential fins arranged along a length of the second sleeve 514A configured to dissipate heat from the damping mechanism 392. The second sleeve 514B is configured as a passive heat exchanger with a number of longitudinal fins arranged around a circumference of the second sleeve 514B configured to dissipate heat from the damping mechanism 392. The second sleeve 514A and the second sleeve 514B represent just two passive heat exchangers with a number of fins configured to dissipate heat from the damping mechanism 392. Instead of the circumferential fins of the second sleeve 514A or the longitudinal fins of the second sleeve 514B, the fins can be, for example, diagonal or helical, crosshatched, or segmented to form pins or more substantial protrusions.

The first sleeve 512 is of a first material having a first thermal conductivity, and the second sleeve 514A or the second sleeve 514B is of a second material having a second thermal conductivity greater than the first thermal conductivity. The first material also has a first specific heat capacity, and the second material also has a second specific heat capacity, which can be greater or less than the first specific heat capacity. The first material of the first sleeve 512 can be a polymer such as polycarbonate, and the second material of the second sleeve 514A or the second sleeve 514B can be a different polymer (e.g., PEI), a metal (e.g., stainless steel, aluminum), or an alloy (e.g., aluminum alloy). A radially oriented thermal gradient, or a thermal gradient vector field, is thereby established from the gasket system 392, through the first sleeve 512, through the second sleeve 514A or the second sleeve 514B, and into a fluid medium (e.g., air within the housing 270) for conducting heat away from the damping mechanism 392.

The thermal conductivity and heat capacity of the heat sink 510A or 510B along with a number of fins, dimensions of the fins, pitch of the fins, or the like of the heat exchanger is sufficient for operating the catheter assembly 160 for at least 1, 2, 3, 4, 5, 10, 15, 20, 25, or 30 minutes for modifying intravascular lesions. Because there can be little convection inside the housing 270 of the catheter assembly 270, the fins of the heat sink 510A or 510B are sized as large as needed to achieve a desired operation time for the catheter assembly 160 while maintaining ease of use for an operator of the catheter assembly 160.

FIG. 6 provides a schematic illustrating a cross-sectional view of the damping mechanism 392 and a fourth heat sink 610 in accordance with some embodiments. The heat sink 610 includes a first annulus 612 at a first end (e.g., proximal end) of the gasket system 392, a second annulus 613 at a second, opposing end (e.g., distal end) of the gasket system 392. The heat sink 610 further includes a number of longitudinal members 616 set in the annuli 612 and 613 around a circumference of the gasket system 392 configured to conduct and dissipate heat from the damping mechanism 392. Optionally, the heat sink 610 further includes a number of struts 617 set in the annuli 612 and 613 radially outward from the number of longitudinal members 616 for additional structural integrity.

The annuli 612 and 613 are of a first material having a first thermal conductivity, and the longitudinal members 616 are of a second material having a second thermal conductivity greater than the first thermal conductivity. The first material also has a first specific heat capacity, and the second material also has a second specific heat capacity, which can be greater or less than the first specific heat capacity. The first material of the annuli 612 and 613 can be a polymer such as polycarbonate, and the second material of the longitudinal members 616 can be a different polymer (e.g., PEI), a metal (e.g., stainless steel, aluminum), or an alloy (e.g., aluminum alloy). The thermal conductivity and heat capacity of the heat sink 610 is such that the catheter assembly 160 can be operated for at least 1, 2, 3, 4, 5, 10, 15, 20, 25, or 30 minutes for modifying intravascular lesions.

The number of struts 617 such as 4, 6, or 8 struts, when present, is sufficient to provide structural integrity without interfering with the efficiency of the longitudinal members 616 in dissipating heat from the damping mechanism 392.

FIG. 7 provides a schematic illustrating a cross-sectional view of the damping mechanism 392 and a fifth heat sink 710 in accordance with some embodiments. The heat sink 710 includes a first sleeve 712 around the gasket system 392 and a second sleeve 714 around the first sleeve 712. The first sleeve 712 includes a fillable cavity 715 formed by a circumferential groove around the first sleeve 712.

The cavity 715 can simply be filled with air. Alternatively, the cavity 715 can be filled, in whole or in part, with a coolant of one or more materials featuring a different specific heat capacity, a different thermal conductivity, or a different specific heat capacity and a different thermal conductivity than air. For example, the coolant can be selected from water, a glycol (e.g., ethylene glycol, diethylene glycol, propylene glycol, etc.), a water-glycol mixture, a mineral oil, a silicone oil, a heat-storage material, and combinations thereof. The heat-storage material can be PX-52 by Rubitherm Technologies GmbH of Berlin, Germany, which includes a phase change material on a solid support (e.g., silica). Heat from the damping mechanism 392 is conducted to the cavity 715 in accordance with a radially oriented thermal gradient and absorbed by the coolant in accordance with its specific heat capacity. With respect to the phase change material, heat from the damping mechanism 392 is absorbed by the phase change material to melt the phase change material instead of increasing the temperature of the heat-storage material. A benefit of the heat-storage material is that it does not melt but rather congeals as a result of the phase change material's attachment to the solid support. This makes the heat-storage material easier to contain in the cavity 715. The second sleeve 714 around the first sleeve 712 provides a seal for the cavity 715 and any contents disposed in the cavity 715.

The first sleeve 712 is of a first material having a first thermal conductivity, and the second sleeve 714 is of a second material optionally having a second thermal conductivity greater than the first thermal conductivity. The first material also has a first specific heat capacity, and the second material also has a second specific heat capacity, which can be greater or less than the first specific heat capacity. The first material of the first sleeve 712 can be a polymer such as polycarbonate, and the second material of the second sleeve 714 can be a same polymer or a different polymer (e.g., PEI), a metal (e.g., stainless steel, aluminum), or an alloy (e.g., aluminum alloy). A radially oriented thermal gradient, or a thermal gradient vector field, can be established from the gasket system 392, through the first sleeve 712, through the cavity 715 including any coolants, through the second sleeve 714, and into a fluid medium (e.g., air within the housing 270) for conducting heat away from the damping mechanism 392. The thermal conductivity and heat capacity of the heat sink 710 is such that the catheter assembly 160 can be operated for at least 1, 2, 3, 4, 5, 10, 15, 20, 25, or 30 minutes for modifying intravascular lesions.

FIG. 8A provides a schematic illustrating a cross-sectional view of the damping mechanism 392 and a sixth heat sink 810 in accordance with some embodiments. The heat sink 810 is an example of a heat sink incorporating a number of features of the heat sinks 510A, 610, and 710. As such, the heat sink 810 includes a first sleeve 812 around the gasket system 392 and a second sleeve 814 fashioned as a passive heat exchanger around the first sleeve 812. The first sleeve 812 includes a fillable cavity 815 formed by a circumferential groove around the first sleeve 812, which can be filled with any coolant set forth herein, and for which the second sleeve 814 provides a seal. In addition, the heat sink 810 includes a number of longitudinal members 816 set in ends of the first sleeve 812 around a circumference of the gasket system 392. The longitudinal members 816 are configured to extend from the heat sink 810 toward the proximal end of the core wire 384 to draw heat away from the heat sink 810. The longitudinal members 816 are also configured to embed in any coolant in the cavity 815. When the coolant is a heat-storage material, the longitudinal members are configured to draw heat away from the heat-storage material such as latent heat when the heat-storage material is in its congealed state, thereby providing stable responses for heat spikes and drawing even more heat away from the damping mechanism 392 when the catheter assembly 160 is deactivated during intermittent breaks in an intravascular-lesion-modifying procedure. Such features, as set forth herein, configure the heat sink 810 to conduct and dissipate heat from the damping mechanism 392. The thermal conductivity and heat capacity of the heat sink 810 is such that the catheter assembly 160 can be operated for at least 1, 2, 3, 4, 5, 10, 15, 20, 25, or 30 minutes for modifying intravascular lesions.

Any heat sink of the heat sinks 410, 510A, 510B, 610, 710, and 810 can be modified in any of a number of ways to increase or decrease operation times for the catheter assembly 160 including the heat sink. This is to balance manufacturing costs with expected procedure times for the catheter assembly 160, which catheter assembly 160 is also a disposable or single-use disposable catheter assembly 160 in some embodiments. Not only can a heat sink of the heat sinks 410, 510A, 510B, 610, 710, and 810 be modified with features of any other heat sink of the heat sinks 410, 510A, 510B, 610, 710, and 810, but materials and dimensions (e.g., relative dimensions) of the heat sink can be modified as well. For example, while the second sleeve 414 of the first heat sink 410 is shown in FIG. 4 as having a same thickness as the first sleeve 412, the second sleeve 414 can be at least 2, 3, 4, or 5 times thicker in some embodiments to increase the heat capacity of the second sleeve 414 and the heat sink 410. An increase in the heat capacity of the second sleeve 414 can alternatively or additionally be accomplished by using a material with a higher specific heat capacity than the example materials given for the second material of the second sleeve 414. For another example, while the cavity 715 is shown as having about half a cross-sectional area, or thickness, of the damping-mechanism bore 398, the cavity 715 can be at least as thick as the damping-mechanism bore 398 or 2, 3, 4, or 5 times thicker than the damping-mechanism bore 398 in some embodiments to increase the heat capacity of the cavity 715 and the heat sink 710. An increase in the heat capacity of the cavity 715 can alternatively or additionally be accomplished by using a coolant with a higher specific heat capacity than the example coolants given for the cavity 715. In general for all heat sinks provided herein, it is desired to keep a temperature below about 200° F. in the housing 270 of the catheter assembly 160 such as between the damping mechanism 392 and the housing 270.

Making the catheter assembly 160 including the sonic connector 385 at the proximal end of the core wire 384, the damping mechanism 392 around the proximal end portion of the core wire 384, and any heat sink of the heat sinks 410, 510A, 510B, 710, and 810 includes molding a cartridge 390 including a damping-mechanism bore 398 in a first sleeve such as the first sleeve 412, 512, 712, or 812; disposing a second sleeve such as the second sleeve 412, 512A, 512B, 712, or 812 over the first sleeve to form the heat sink including the first and second sleeves; disposing the core wire 384 through a center of the damping-mechanism bore 398 coincident with a rotational axis of the cartridge 390; disposing the number of O-rings in the damping-mechanism bore 398 around the core wire 384; and fixing the retainer 396 in a proximal end of the damping-mechanism bore 398 to form the damping mechanism 392 around the core wire 384. For the heat sink 610, the steps of molding the cartridge 390 with the first sleeve and disposing the second sleeve over the first sleeve are modified such that molding the cartridge 390 includes molding the cartridge 390 including the second annulus 613; molding the first annulus 612; and disposing or otherwise setting at least the number of longitudinal members 616 in the annuli 612 and 613 to form the damping-mechanism bore 398, or an analog thereof, and the heat sink 610.

Molding the cartridge 390 includes molding the cartridge 390 by way of compression molding, injection molding, thermoforming, or a combination thereof.

Prior to disposing the core wire 384 through the center of the damping-mechanism bore 398, the core wire 384 is optionally disposed in a heat-shrinkable polymeric sleeve (e.g., polytetrafluoroethylene ["PTFE"]) and uniformly heated to shrink the heat-shrinkable polymeric sleeve around the core wire 384 to form the polymeric sleeve 386 around the core wire 384.

Fixing the retainer 396 in the proximal end of the damping-mechanism bore 398 generates a radial compressive force on the core wire 384. The radial compressive force occurs from an axial compressive force on the O-rings resulting from axially pressing the O-rings against a distal end of the damping-mechanism bore 398 with the retainer 396 in the proximal end of the damping-mechanism bore 398. The axial compressive force, in turn, generates the radial compressive force on the core wire 384 via radial expansion of the O-rings, thereby, radially pressing the O-rings against an inner wall of the damping-mechanism bore 398 opposing the core wire 384 and the core wire 384 itself. The compressive force is sufficient for damping a number of degrees of freedom of vibrational energy in the proximal end portion of the core wire 384. Heat from the damping dissipates through the heat sink.

Making the catheter assembly 160 includes molding a housing of the catheter assembly 160, and subsequently disposing the cartridge 390 including the damping mechanism 392 around the core wire 384 in the housing to form the catheter assembly 160. Disposing the cartridge 390 in the housing includes connecting the sonic connector 385 of the core wire 384 to the ultrasound-producing mechanism configured to impart the vibrational energy to the proximal end of the core wire 384.

Advantages of some embodiments of the catheter assembly 160 include, but are not limited to, passive control of heat caused by damping vibrational energy; running times sufficient for modifying intravascular lesions either by crossing, ablating, or a combination of crossing and ablating the intravascular lesions; use of polymers (e.g., polycarbonate) suitable for use in molding such as injection molding; or a combination thereof. Such advantages make possible single-use disposable catheter assemblies such as some embodiments of the catheter assembly 160.

While some particular embodiments have been provided herein, and while the particular embodiments have been provided in some detail, it is not the intention for the particular embodiments to limit the scope of the concepts presented herein. Additional adaptations and/or modifications can appear to those of ordinary skill in the art, and, in broader aspects, these adaptations and/or modifications are encompassed as well. Accordingly, departures may be made from the particular embodiments provided herein without departing from the scope of the concepts provided herein.

What is claimed is:

1. A catheter assembly for modifying intravascular lesions, comprising:
    a sonic connector at a proximal end of a core wire, the sonic connector configured to couple to an ultrasound-producing mechanism and transmit vibrational energy to the proximal end of the core wire, which core wire includes a distal end portion;
    a damping mechanism including a gasket system around a proximal end portion of the core wire in a damping-mechanism bore of the catheter assembly, the damping mechanism configured to damp the vibrational energy; and
    a heat sink connected to the damping mechanism, wherein:
        the heat sink includes a first sleeve around the gasket system and a second sleeve around the first sleeve; and
        the first sleeve includes a cavity formed by a circumferential groove around the first sleeve, the cavity is filled with coolant, and the second sleeve is disposed over the cavity.

2. The catheter assembly of claim 1, wherein the first sleeve is of a first material having a first thermal conductivity and the second sleeve is of a second material having a second thermal conductivity greater than the first thermal conductivity.

3. The catheter assembly of claim 2, wherein the second sleeve is configured as a passive heat exchanger, the heat exchanger including a plurality of circumferential fins arranged along a length of the second sleeve configured to dissipate the heat from the damping mechanism.

4. The catheter assembly of claim 2, wherein the second sleeve is configured as a passive heat exchanger, the heat exchanger including a plurality of longitudinal fins arranged around a circumference of the second sleeve configured to dissipate the heat from the damping mechanism.

5. The catheter assembly of claim 1, wherein the coolant is water, a glycol, a water-glycol mixture, a mineral oil, a silicone oil, or a heat-storage material.

6. The catheter assembly of claim 1, wherein the heat sink includes a first annulus at a first end of the gasket system, a second annulus at a second, opposing end of the gasket system, and a plurality of longitudinal members arranged around a circumference of the gasket system.

7. The catheter assembly of claim 1, wherein a center of the gasket system is positioned over a vibrational node of the core wire where the core wire experiences less transverse-wave-producing vibrational energy than an anti-node of the core wire, thereby reducing frictional heating.

8. The catheter assembly of claim 1, wherein the gasket system includes a plurality of axially and radially compressed O-rings in the damping-mechanism bore.

9. The catheter assembly of claim 1, further comprising at least a portion of an ultrasound-producing mechanism including an ultrasound transducer.

10. A system for modifying intravascular lesions, comprising:
    a catheter assembly including:
        a sonic connector at a proximal end of a core wire, the sonic connector configured to transmit vibrational energy to the proximal end of the core wire, which core wire includes a distal end portion;
        a damping mechanism including a gasket system around a proximal end portion of the core wire in a damping-mechanism bore of the catheter assembly, the damping mechanism configured to damp the vibrational energy; and
        a heat sink connected to the damping mechanism, wherein:
            the heat sink includes a first sleeve around the gasket system and a second sleeve around the first sleeve; and
            the first sleeve includes a cavity formed by a circumferential groove around the first sleeve, the cavity is filled with coolant, and the second sleeve is disposed over the cavity; and
    an ultrasound-producing mechanism including:
        an ultrasound generator; and
        an ultrasound transducer.

11. The system of claim 10, wherein the first sleeve of a first material having a first thermal conductivity and the second sleeve of a second material having a second thermal conductivity greater than the first thermal conductivity.

12. The system of claim 11, wherein the second sleeve is configured as a passive heat exchanger, the heat exchanger including a plurality of circumferential fins arranged along a length of the second sleeve configured to dissipate the heat from the damping mechanism.

13. The system of claim 11, wherein the coolant is selected from water, a glycol, a water-glycol mixture, a mineral oil, a silicone oil, and a heat-storage material.

14. The system of claim 10, wherein the heat sink includes a first annulus at a first end of the gasket system, a second annulus at a second, opposing end of the gasket system, and a plurality of longitudinal members arranged around a circumference of the gasket system.

15. The system of claim 10, wherein the gasket system includes a plurality of axially and radially compressed O-rings in the damping-mechanism bore.

16. The system of claim 10, further comprising a console including a foot switch and the ultrasound-producing mechanism including the ultrasound generator and the ultrasound transducer, wherein the foot switch is configured to activate and deactivate the ultrasound-producing mechanism.

17. The system of claim 10, further comprising a console including a foot switch and the ultrasound generator of the ultrasound-producing mechanism, wherein the catheter assembly further includes the ultrasound transducer of the ultrasound-producing mechanism, and the foot switch is configured to activate and deactivate the ultrasound-producing mechanism.

\* \* \* \* \*